United States Patent [19]

Bolmer et al.

[11] Patent Number: 5,099,081
[45] Date of Patent: * Mar. 24, 1992

[54] SOLVENT EXTRACTION OF I-365 FROM I-141B

[75] Inventors: Michael S. Bolmer, Lower Providence; Maher Y. Elsheikh, Tredyffrin, both of Pa.

[73] Assignee: Atochem North America, Inc., Philadelphia, Pa.

[*] Notice: The portion of the term of this patent subsequent to Mar. 24, 2009 has been disclaimed.

[21] Appl. No.: 751,014

[22] Filed: Aug. 28, 1991

[51] Int. Cl.$^5$ ............................................. C07C 17/38
[52] U.S. Cl. .................................................... 570/180
[58] Field of Search ........................................ 570/180

[56] References Cited

U.S. PATENT DOCUMENTS 3,624,166  11/1971  Fuhrmann et al. ............... 570/180
3,947,558  3/1976   Eijl ................................... 570/180
4,031,148  6/1977   Helgorsky .

*Primary Examiner*—Alan Siegel

[57] ABSTRACT

Partial or total separation of a mixture of 1,1,1,3,4-pentafluorobutane and 1,1-dichloro-1-fluoroethane by liquid-liquid extraction with methanol based solvent mixtures, such as methanol with ethanolamine or ethylene glycol.

3 Claims, 2 Drawing Sheets

SOLVENT EXTRACTION OF I-365 FROM I-141B

FIELD OF THE INVENTION

This invention relates to a method of partially or totally separating a mixture of 1,1,1,3,3-pentafluorobutane ("I-365") and 1,1-dichloro-1-fluoroethane ("I-141b") by liquid-liquid extraction with methanol-based solvent mixtures.

BACKGROUND OF THE INVENTION

I-365, a solvent and precursor for other chemicals, is a byproduct formed during the manufacture of I-141b, a replacement for trichlorofluoromethane as a blowing agent. Since commercial specifications for I-141b normally call for 99.5% purity, a method for I-365 removal is needed, desirably to levels below 0.5%. Separation by conventional distillation means is extremely difficult, however, since I-365 and I-141b form an azeotrope.

While liquid-liquid extraction has been reported in U.S. Pat. No. 4,031,148 for separating chlorinated hydrocarbons by the use of water-miscible solvents and 0-50% water, applicant is not aware of literature which discloses liquid-liquid extraction for separating HFC's (hydrofluorocarbons) such as I-365 from HCFC's (hydrochlorofluorocarbons) such as I-141b. Also, as noted in column 1, lines 53-56 of said U.S. Pat. No. 4,031,148, and as demonstrated by copending application Ser. No. 751,023, filed on even date herewith, it is impossible to foresee which extraction agents will enable the separation of any two substances.

SUMMARY OF THE INVENTION

A method is provided for at least partial separation of a mixture of I-365 and I-141b comprising liquid-liquid extraction on the mixture in the presence of a solvent containing methanol in admixture with ethylene glycol, ethanolamine, propylene glycol, dipropylene glycol and water, or mixtures thereof, preferably with ethanolamine or ethylene glycol. More specifically, the process comprises contacting the mixture of I-141b and I-365 with the extracting agent such that the agent extracts I-365 from the mixture and forms a separate phase therefrom, then separating the phases of I365-rich solvent and I-141b/I-365 mixture, which mixture now has a correspondingly reduced concentration of I-365.

DETAILED DESCRIPTION OF THE INVENTION

It has now been discovered that efficient separation of I-365 and I-141b can be achieved via liquid-liquid extraction using the aforementioned methanol-based solvent mixtures. Methanol itself is ineffective. The solvent mixtures are found to have a selectivity for I-365 (at 25° C.) of from about 1.24 to 1.89.

The exact proportion of solvent components in the mixture is not critical, although solvent mixtures containing about 25-50 mole percent of methanol are generally preferred from the standpoint of phase separation.

Figure 1:
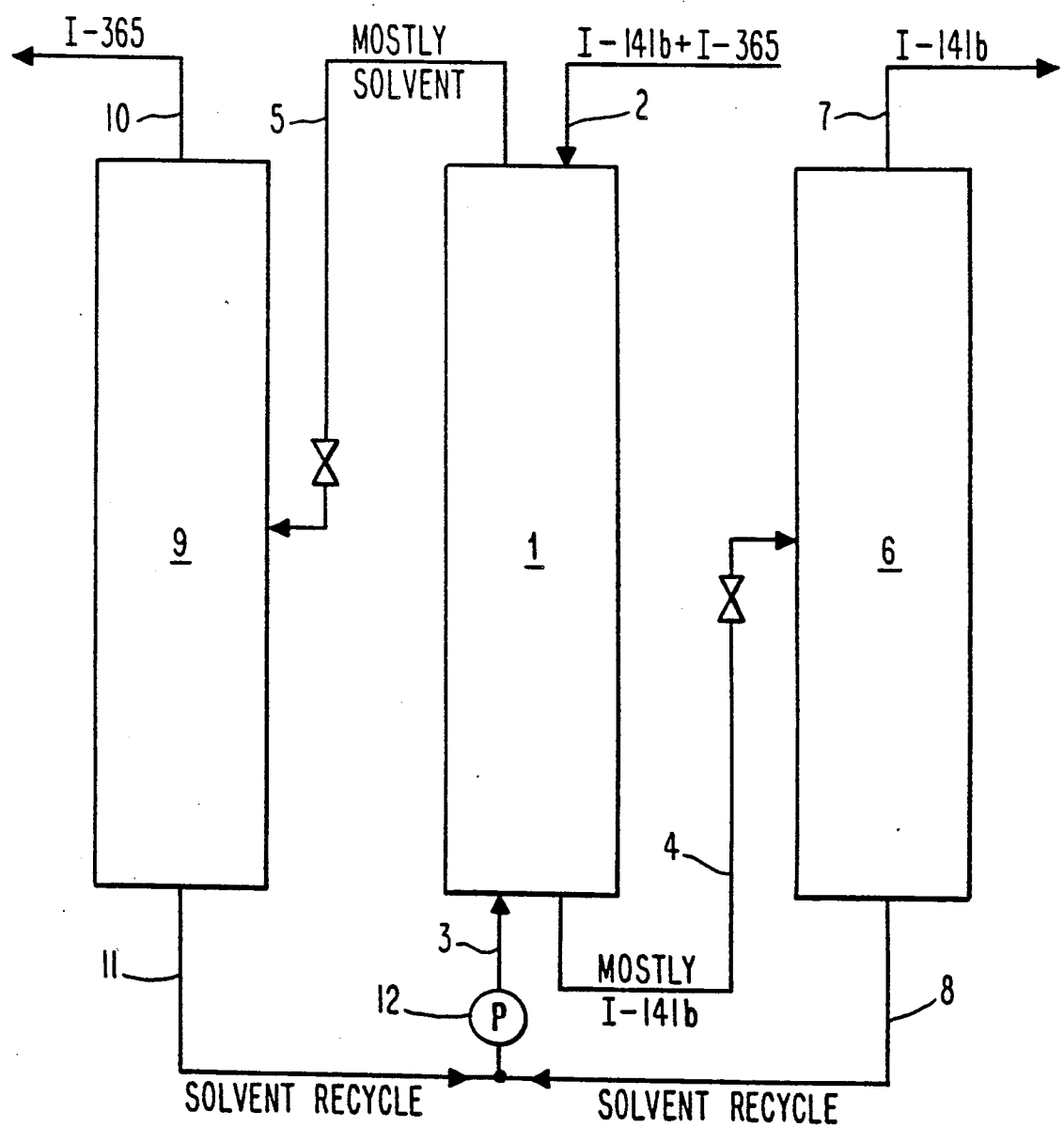
FIG. 1 is a schematic illustration of a liquid-liquid, extraction system.

The separation can be carried out in a liquid-liquid extractor, as shown in FIG. 1, where a I-141b/I-365 mixture is shown as the heavier component entering the top of the extraction column 1 through line 2. The solvent, shown as the lighter component, enters column 1 at the bottom through line 3 (for a solvent which is heavier, the two feed streams would come in the reversed ends). The purified (or partially purified) I-141b stream is removed from the bottom of column 1 through line 4, and the used, I365-enriched, solvent stream is removed from the top of column 1 through line 5. Any solvent adsorbed into the I-141b stream is removed by distillation in column 6, producing a purified I-141b stream which exits the top of column 6 through line 7 and a small solvent recycle stream which exits the bottom of column 6 through line 8 for reintroduction to column 1. The used solvent stream is distilled in distillation column 9 to remove the I-365 (and any I-141b) which exits at the top of column 9 through line 10, and then the purified solvent stream is recycled back to column 1 via line 11. A pump 12 provides the power to circulate the solvent around the process.

Figure 2:
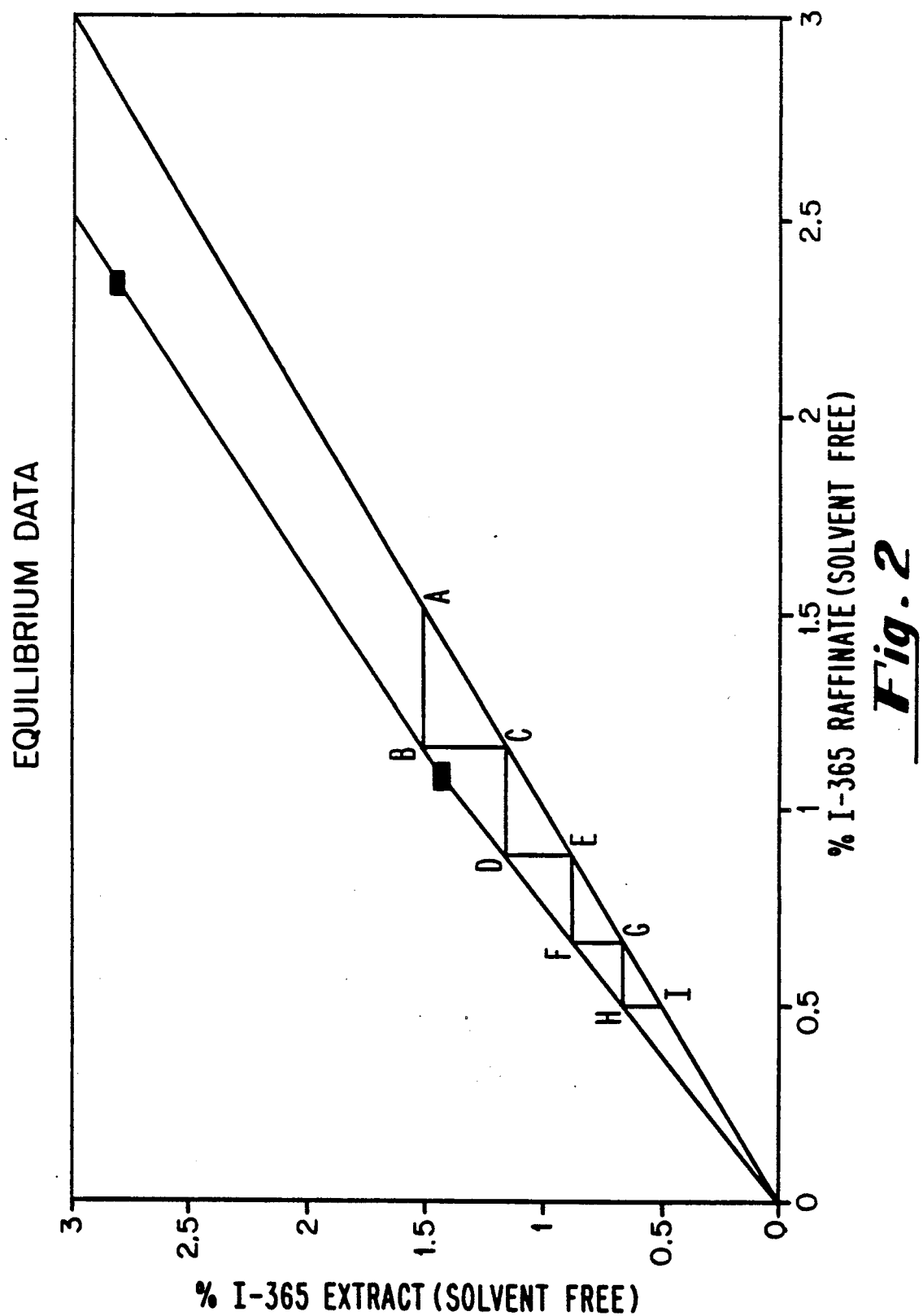
FIG. 2 shows equilibrium data at 25° C. for the ternary system of I-365, I-141b, and methanol/ethanolamine solvent, and the use of such data for determining equilibrium stages.

The extraction column can be designed from equilibrium data. For example, the Table below shows equilibrium concentrations for the ternary system of I-365, I-141b, and ethanolamine/methanol (2:1) at 25° C. Plotting of the data as in FIG. 2 enables the design of an extraction column to reduce I-365 in a I-141b stream from, for example, 1.5% to 0.5%. Referring to FIG. 2, the I-141b is fed to an extraction column (at point A). The solvent leaves the column (at point B) with 1.5% I-365, in equilibrium with I-141b now having an I-365 concentration of only 1.2% (point C). Thus, after leaving the first equilibrium stage of the extraction column (from point A to point C), the I-365 concentration has been reduced from 1.5% to 1.2%. Using the same procedure (C to E, E to G, and G to I), it is seen that the concentration can be reduced to 0.5% in just four equilibrium stages.

Table

| | Equilibrium Data for I-141b, I-365, and Solvent at 25° C. (in Mole %) | | |
|---|---|---|---|
| I-141b | I-365 (*) | Ethanolamine | Methanol |
| (A) RAFFINATE | | | |
| 96.9 | 1.1 (1.1) | 0.0 | 2.0 |
| 95.3 | 2.3 (2.3) | 0.0 | 2.4 |
| 91.4 | 6.1 (6.2) | 0.0 | 2.5 |
| 88.8 | 8.9 (9.1) | 0.0 | 2.3 |
| (B) EXTRACT | | | |
| 30.5 | 0.4 (1.4) | 44.4 | 24.6 |
| 24.3 | 0.7 (2.8) | 50.6 | 24.4 |
| 26.7 | 2.2 (7.5) | 50.0 | 21.1 |
| 29.1 | 3.4 (10.4) | 45.7 | 21.7 |

(*) Amounts in Parenthesis Show I-365 On A Solvent-Free Basis

What is claimed is:

1. A method of at least partial separation of a mixture of 1,1,1,3,3-pentafluorobutane and 1,1-dichloro-1-fluoroethane comprising liquid-liquid extraction on said mixture in the presence of an extraction agent containing methanol in admixture with ethylene glycol, ethanolamine, propylene glycol, dipropylene glycol and water, or mixtures thereof.

2. The method of claim 1 wherein the extraction agent is a methanol/ethanolamine mixture.

3. The method of claim 1 wherein the extraction agent is a methanol/ethylene glycol mixture.

* * * * *